(12) United States Patent
Jensen-Jarolim et al.

(10) Patent No.: US 8,420,095 B2
(45) Date of Patent: Apr. 16, 2013

(54) ANTIGEN-CONTAINING MICROSPHERES FOR THE TREATMENT OF ALLERGIES

(75) Inventors: Erika Jensen-Jarolim, Vienna (AT); Franziska Roth-Walter, Vienna (AT); Franz Gabor, Vienna (AT)

(73) Assignee: Biomay Produktions-und Handels AG, Vienna (AU)

( * ) Notice: Subject to any disclaimer, the term of this patent is extended or adjusted under 35 U.S.C. 154(b) by 1059 days.

(21) Appl. No.: 10/562,066

(22) PCT Filed: Apr. 28, 2004

(86) PCT No.: PCT/EP2004/004480
§ 371 (c)(1),
(2), (4) Date: Mar. 23, 2007

(87) PCT Pub. No.: WO2005/000274
PCT Pub. Date: Jan. 6, 2005

(65) Prior Publication Data
US 2007/0275079 A1    Nov. 29, 2007

(30) Foreign Application Priority Data
Jun. 27, 2003   (DE) .................................. 103 29 087

(51) Int. Cl.
*A61K 38/00* (2006.01)
*A61K 39/00* (2006.01)
*A61K 39/35* (2006.01)
*A61K 39/36* (2006.01)
*A61K 39/38* (2006.01)
*C07K 2/00* (2006.01)
*C07K 4/00* (2006.01)
*C07K 5/00* (2006.01)
*C07K 7/00* (2006.01)
*C07K 14/00* (2006.01)
*C07K 16/00* (2006.01)
*C07K 17/00* (2006.01)

(52) U.S. Cl.
USPC .................. 424/184.1; 424/185.1; 424/274.1; 424/275.1; 530/300

(58) Field of Classification Search ........................ None
See application file for complete search history.

(56) References Cited

U.S. PATENT DOCUMENTS

| | | | | |
|---|---|---|---|---|
| 4,833,092 | A | * | 5/1989 | Geysen .......................... 436/501 |
| 6,326,201 | B1 | * | 12/2001 | Fung et al. ..................... 435/377 |
| 6,610,535 | B1 | * | 8/2003 | Lu et al. ......................... 435/325 |
| 7,736,857 | B2 | * | 6/2010 | Denny et al. ..................... 435/7.1 |
| 2006/0251580 | A1 | * | 11/2006 | Keppler et al. ............. 424/1.49 |
| 2006/0263825 | A1 | * | 11/2006 | Denny et al. ..................... 435/7.1 |

FOREIGN PATENT DOCUMENTS

| | | |
|---|---|---|
| DE | 4120760 A1 | 3/1993 |
| DE | 68926828 T2 | 1/1997 |
| DE | 69712110 T2 | 12/2002 |
| EP | 0333523 B1 | 7/1996 |
| EP | 0 7 738 890 A1 | 10/1996 |
| EP | 1 356 826 A1 | 10/2003 |
| WO | 9300076 A1 | 1/1993 |
| WO | 9801161 A2 | 1/1998 |

OTHER PUBLICATIONS

Blumenthal et al. 'Definition of an Allergen.' Allergens and Allergen Immunotherapy. Ed. R Lockey, S. Bukantz and J. Bousquet. New York: Marcel Decker, 2004.37-50.*
Kinnunen et al. 'Potential/of/an altered peptide ligand of lipocalin allergen Bos d 2 for peptide immunotherapy.' J. Allergy Clin Immunol. 119(4):965-972, 2007.*
Brayden et al. 'Keynote review: Intestinal Peyer's patch M cells and oral vaccine targeting.' DDT 10(17):1145-1157, 2005.*
Azizi et al. 'Enhancing Oral Vaccine Potency by Targeting Intestinal M Cells.' PLOS Pathogens. 6(11);1-7, 2010.*
Walter et al. 'Functionalisation of allergen-loaded microspheres with wheat germ agglutinin for targeting enterocytes.' Biochem. Biophys. Res. Comm. 315:281-287, 2004.*
Giannasca et al. 'Regional differences in glycoconjugates of intestinal M cells in mice: potential targets for mucosal vaccines.' Am. J. Physiol. 30:G1108-G1121, 1994.*
Roth-Walter et al. 'M cell targeting with *Aleuria aurantia* lectin as a novel approach for oral allergen immunotherapy.' J. Allergy. Clin. Immunol. 114:1362-1368, 2004.*
Suphioglu et al. 'What are the important allergens in grass pollen that are linked to human allergic disease?' Clin. Exp. Allerg. 30:1335-1341, 2000.*
Gupta, R. K. et al., "Determination of protein loading in biodegradable polymer microspheres containing tetanus toxid", Vaccine, vol. 15, No. 67, pp. 672-678, 1997.
Brooking, J. et al., "Transport of Nanoparticles Across the Rat Nasal Mucosa", Journal of Drug Targeting, 2001, vol. 9, No. 4, pp. 267-279.
Clark, M. A. et al. "Lectin-mediated mucosal delivery of drugs and microparticles", Advanced Drug Delivery Reviews 43 (2000) 207-233.
Vasir et al., Bioahesive microspheres as a controlled drug-delivery system, Int. J. Pharmaceutics. 2003; 255: 13-32.
Hussain et al., Enhanced Oral Uptake of Tomato-Lectin Conjugated Nanoparticles in the Rat; Pharmaceut. Res. 1997; 14(5): 613-18.
Ertl et al., Lectin-Mediated Bioadhesion: Preparation, Stability, and Caco-2 Binding of Wheat Germ Agglutinin-Functionalized Poly(D,L-lactic-co-glycolic acid) Microspheres. J. Drug Targeting. 2000; 8: 173-84.

* cited by examiner

*Primary Examiner* — Nora Rooney
(74) *Attorney, Agent, or Firm* — Milbank, Tweed, Hadley & McCloy LLP

(57) ABSTRACT

Microspheres containing antigens for allergy therapy, the microspheres having a binding constant of $1 \times 10^4 \, M^{-1}$ toward a specific carbohydrate residue of intestinal and/or nasal epithelial cells.

11 Claims, 4 Drawing Sheets

```
                        SEQUENCE LISTING

<160> NUMBER OF SEQ ID NOS: 17

<210> SEQ ID NO 1
<211> LENGTH: 12
<212> TYPE: PRT
<213> ORGANISM: Artificial Sequence
<220> FEATURE:
<223> OTHER INFORMATION: From Grass Pollen Allergen Phl p 5

<400> SEQUENCE: 1

Cys Ser Arg Leu Gly Arg Ser Ser Ala Trp Val Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: From Grass Pollen Allergen Phl p 5

<400> SEQUENCE: 2

Cys Thr His Trp Gln Leu Gly Glu Arg Pro Asp Cys
1               5                   10

<210> SEQ ID NO 3
<211> LENGTH: 12
<212> TYPE: PRT
<213> ORGANISM: Artificial Sequence
<220> FEATURE:
<223> OTHER INFORMATION: From Grass Pollen Allergen Phl p 5

<400> SEQUENCE: 3

Cys Pro Ser Thr Pro Gly Glu Arg Val Arg His Cys
1               5                   10
```

```
<210> SEQ ID NO 4
<211> LENGTH: 12
<212> TYPE: PRT
<213> ORGANISM: Artificial Sequence
<220> FEATURE:
<223> OTHER INFORMATION: From Grass Pollen Allergen Phl p 5

<400> SEQUENCE: 4

Cys Arg Gly Gly Pro Asp Asp Leu Thr Ala Leu Cys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: From Grass Pollen Allergen Phl p 5

<400> SEQUENCE: 5

Cys Pro Phe Trp Val Arg Gly Thr Thr Asp Trp Cys
1               5                   10

<210> SEQ ID NO 6
<211> LENGTH: 7
<212> TYPE: PRT
<213> ORGANISM: Artificial Sequence
<220> FEATURE:
<223> OTHER INFORMATION: From Grass Pollen Allergen Phl p 5

<400> SEQUENCE: 6

Cys Gln Val Gly Pro Glu Cys
1               5

<210> SEQ ID NO 7
<211> LENGTH: 12
<212> TYPE: PRT
<213> ORGANISM: Artificial Sequence
<220> FEATURE:
<223> OTHER INFORMATION: From Grass Pollen Allergen Phl p 5

<400> SEQUENCE: 7

Cys Pro Ser Thr Pro Gly Ser Arg Gln Asn Met Cys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: From Grass Pollen Allergen Phl p 5

<400> SEQUENCE: 8

Cys Pro Ser Thr Pro Gly Asp Asn Pro Leu Val Cys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: From Grass Pollen Allergen Phl p 5

<400> SEQUENCE: 9

Cys Lys Phe Val Val Asn Gly Arg Trp Ile Asp Cys
1               5                   10

<210> SEQ ID NO 10
<211> LENGTH: 12
```

```
<212> TYPE: PRT
<213> ORGANISM: Artificial Sequence
<220> FEATURE:
<223> OTHER INFORMATION: From Grass Pollen Allergen Phl p 5

<400> SEQUENCE: 10

Cys Lys Phe Leu Val Asn Gly Arg Trp Ile Asp Cys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: From Grass Pollen Allergen Phl p 5

<400> SEQUENCE: 11

Cys Arg Leu Thr Glu Asn Thr Glu Pro Leu Leu Cys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: From Grass Pollen Allergen Phl p 5

<400> SEQUENCE: 12

Cys Phe Thr Trp Gly Gly Leu Arg Asp Lys Ser Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: From Grass Pollen Allergen Phl p 5

<400> SEQUENCE: 13

Cys Glu Arg Ala Gly Ala Met Glu Arg Ala Asn Cys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: From Grass Pollen Allergen Phl p 5

<400> SEQUENCE: 14

Cys Arg Ser Val Ser Lys Glu Glu Pro Gly Met Cys
1               5                   10

<210> SEQ ID NO 15
<211> LENGTH: 12
<212> TYPE: PRT
<213> ORGANISM: Artificial Sequence
<220> FEATURE:
<223> OTHER INFORMATION: From Grass Pollen Allergen Phl p 5

<400> SEQUENCE: 15

Cys Lys Leu Gly Lys Phe Gly Ala Ala Arg Val Cys
1               5                   10

<210> SEQ ID NO 16
<211> LENGTH: 12
<212> TYPE: PRT
<213> ORGANISM: Artificial Sequence
```

```
<220> FEATURE:
<223> OTHER INFORMATION: From Grass Pollen Allergen Phl p 5

<400> SEQUENCE: 16

Cys Val Gln Asp Leu Met Lys Ser Ser Gly Val Cys
1               5                   10

<210> SEQ ID NO 17
<211> LENGTH: 12
<212> TYPE: PRT
<213> ORGANISM: Artificial Sequence
<220> FEATURE:
<223> OTHER INFORMATION: From Birch Pollen Allergen Bet v 1

<400> SEQUENCE: 17

Cys Arg Ser Asp Lys Asp Gly Trp Arg Leu Trp Cys
1               5                   10
```

ANTIGEN-CONTAINING MICROSPHERES FOR THE TREATMENT OF ALLERGIES

This application contains a Sequence Listing which has been submitted in electronic format in lieu of a printed paper copy, and is hereby incorporated by reference in its entirety. Said electronic format, created on Oct. 30, 2009, contains 4.15 kB file named 3748800800_ST25.txt.

The present invention relates to microspheres containing antigens, in particular allergens, and being used for allergy therapy.

About 20% of the population suffer from IgE-mediated allergies, which can involve symptoms ranging from milder ones such as hay fever to serious episodes of asthma or anaphylactic shock. In these patients, mast cells and other effector cells of allergy are loaded with IgE antibodies. Upon contact with the allergen the cells can be triggered, that is, mediators are released such as histamine, which is responsible for the allergic symptoms.

The current standard method of allergy treatment is so-called hyposensitization with natural extracts of allergens, which leads to suppression of the symptoms after prolonged treatment. The mechanism of action is not yet completely clear, but an induction of IgG antibodies which can act as blocking antibodies is observed. Furthermore, a modulation of the Th response after prolonged therapy is being discussed.

To make the often readily soluble allergens better immunogenic, so-called adjuvants are used as a rule, such as aluminum trihydroxide. The latter adsorbs the allergen protein and thereby increases its immunogenicity.

As a further possibility for application, the literature describes so-called micro- or nanoparticles containing immunogenic substances. For example, Johansen et al. describe controlled antigen delivery by means of microspheres of poly (lactic-co-glycolic acid) copolymers (so-called PLGA microparticles).

The application of allergens is mostly done subcutaneously or intramuscularly. Some literature sources report experiments with an oral allergy therapy (European Journal of Allergy and Clinical Immunology, WHO Position Paper 44; 53:20-21). Sublingual immunotherapy is already in clinical application, but with moderate success (Rakoski J, Wessner D, Int. Arch. Allergy Immunol. 2001, November; 126(3):185-7).

However, the oral administration of immunogenic substances, incorporated into microspheres, is also known. For instance, K. J. Maloy et al. describe the induction of a mucosal and systemic immune response by oral administration of ovalbumin incorporated into PLGA microparticles (K. J. Maloy et al., Immunology 1994, April, 81(4):661-7). Further, an article by Pecquet et al. has shown that a lactic acid allergen incorporated into PLGA microspheres can be given to mice orally for prophylaxis of milk allergy (Pecquet et al., Vaccine 2000, 18:1196-1202).

Unfortunately, the previous methods of treatment for allergies are not always successful, sometimes a worsening of symptoms is observed, and there are data showing that hyposensitization can even activate IgE synthesis. This may be due to the use of aluminum trihydroxide ($Al(OH)_3$) as an adjuvant, a common adjuvant for many vaccines. Animal experiments have long since shown that aluminum trihydroxide even promotes a Th2 response, i.e. causes IgE formation and thus allergization. This results in the paradoxical situation of allergic patients being immunized with an allergizing adjuvant in combination with allergen extracts. In addition, repeated administrations of increasing amounts of allergen are required, at first even at weekly intervals, which patients frequently find bothersome. Oral administrations of the antigen would permit the patient to do this advantageously at home in the manner of an oral vaccination.

Accordingly, it is the problem of the present invention to provide suitable substances, in particular allergens, for allergy therapy in a form that avoids the above-mentioned disadvantages of known mode of administration of allergens and permits a more reliable response in the patient.

The invention is based on the finding that such a form of administration develops a good effect in particular when the microspheres release their substances on their target tissue in target-specific fashion and over a long time period.

The subject matter of the present invention is therefore microspheres for allergy therapy containing antigens and/or DNA of antigens, in particular allergens and/or DNA of allergens, which are characterized in that the microspheres have a binding constant $K_B$ of at least $1 \times 10^3 \, M^{-1}$, preferably at least $1 \times 10^4 \, M^{-1}$ and most preferably at least $6 \times 10^4 \, M^{-1}$, toward the specific carbohydrate residue, preferably alpha-L-fucose, of intestinal and/or nasal epithelial cells.

Antigens are understood in this invention to mean not only substances recognized as foreign by the organism and triggering an immune response or reacting with an antibody or T cell receptors, but also the derivatives thereof. Besides the allergens defined below, in particular the following antigens are preferred: viral, bacterial, protozoan antigens as well as toxins and worm antigens.

It is preferred that not only antigens can be enclosed in the microspheres, but also the DNA of antigens. It is also possible to incorporate antigens or DNA of antigens into the microspheres alone or jointly. It is preferred that the antigens are allergens. Further, it is preferred that the allergens and/or the DNA of allergens are incorporated into the microspheres.

The term "microspheres" refers here to particles of preferably globular or spherical structure. Since the solvent used for the polymer in producing the microspheres evaporates, the microspheres precipitate out, thereby enclosing cosprayed antigens.

The term "nanoparticles" or "nanospheres" frequently used in the literature is thus likewise subsumed under the term "microspheres" or "microparticles".

The term "allergen" refers not only to naturally occurring allergen extracts and allergen molecules but also to mutants of allergens, hypoallergens or parts of allergen molecules, such as peptides or also allergen mimotopes. Allergen mimotopes can likewise be peptides, such as peptides with an amino acid sequence length of 5 to 25 amino acids. Allergens are able here to trigger an allergy, that is, an immediate-type hypersensitivity reaction, which is induced by the synthesis of IgE antibodies. Hypoallergens are natural or recombinant derivatives of an allergen molecule which, due to slight differences compared with the amino acid sequence of the allergen, assume a conformation by which IgE-binding properties are lost.

In particular, the following allergens are preferred for microspheres: birch pollen (Bet v 1), carrot (Dau c 1), celery (Api g 1), hazelnut (Cor a 1), alder pollen (Aln g 1) and grass pollen (including Phl p 5, Phl p1, Phl p 6, Phl p 7) as well as house dust mite (Der p 1, Der p 2) and fish (parvalbumin).

In particular, the following mimotopes of the allergen Phl p 5 are preferred:

C S R L G R S S A W V C        (SEQ ID NO: 1)

C T H W Q L G E R P D C        (SEQ ID NO: 2)

```
CPSTPGERVRHC      (SEQ ID NO: 3)

CRGGPDDLTALC      (SEQ ID NO: 4)

CPFWVRGTTDWC      (SEQ ID NO: 5)

CQVGPEC           (SEQ ID NO: 6)

CPSTPGSRQNMC      (SEQ ID NO: 7)

CPSTPGDNPLVC      (SEQ ID NO: 8)

CKFVVNGRWIDC      (SEQ ID NO: 9)

CKFLVNGRWIDC      (SEQ ID NO: 10)

CRLTENTEPLLC      (SEQ ID NO: 11)

CFTWGGLRDKSC      (SEQ ID NO: 12)

CERAGAMERANC      (SEQ ID NO: 13)

CRSVSKEEPGMC      (SEQ ID NO: 14)

CKLGKFGAARVC      (SEQ ID NO: 15)

CVQDLMK5SGVC      (SEQ ID NO: 16)
```

In particular, the following mimotope of the allergen Bet v 1 is preferred:

```
CRSDKDGWRLWC      (SEQ ID NO: 17)
```

In all cases there is disulfide bridge formation between the terminal cysteines. The mimotopes were selected by means of a random peptide 10-mer phage library (Mazzucchelli et al., Mazzucchelli, L., Burritt, J. B., Jesaitis, A. J., Nusrat, A., Liang, T. W., Gewirtz, A. T., Schnell, F. J., and Parkos, C. A. Cell-specific peptide binding by human neutrophils. Blood, 93: 1738-1748, 1999) by means of human specific IgE against Phl p 5 or Bet v 1.

The structure of the microspheres permits the antigens and/or DNA of antigens, in particular allergens and/or DNA of allergens, contained in the microspheres to be released slowly and uniformly. An advantage of this continuous release of antigen, in particular allergen, is that it is unnecessary to administer repeated doses of increasing amounts of antigen, in particular allergen, as in conventional hyposensitization. The above of course also applies to the release of DNA of antigens or DNA of allergens.

The adhesiveness of the microspheres to mucosal target tissue is quantified by their adhesiveness to Caco-2 cells.

Caco-2 cells (American Type Culture Catalogue No. HTB-37) are intestinal epithelial cells with high differentiation (polarized growth, microvilli, formation of tight junctions), originally isolated from a human colonic carcinoma. They have surface properties representative of the intestinal epithelium and are therefore suited for studying the adhesiveness of microparticles. For this purpose, fluorescence-labeled (FITC cadaverine) microparticles are produced by covalently binding fluorescein cadaverine through the free carboxyl group of the polymer by the carbodiimide activation method and spraying this compound to form microspheres in the spray drying system. The microspheres are preferably functionalized with a desired lectin (see below) and then incubated with the Caco-2 cells at preferably 4° C. The temperature of 4° C. is selected to eliminate internalization into the epithelial cells by endocytosis processes and to assess purely bonding ability. After abundant washing with ice-cold phosphate buffer to subtract non-specific bonds, the cell-bound microparticles are dissolved together with the Caco-2 cells, and the fluorescence contained in the sample is determined in a fluorescence spectrometer.

Preferably, the inventive microspheres have substances on their surface that increase adhesiveness to mucosal cells and are nontoxic to humans.

These substances located on the surface of the microspheres serve not only to improve adhesion, but also to select the mucosal target tissue. In allergen therapy it is further desirable that the substances on the surface of the microspheres are nontoxic to humans and thus do not cause any harmful side effects.

Further, the substances on the microsphere surface are preferably lectins. It is preferred that the lectins are nontoxic. It is particularly preferred that the lectins are edible.

Lectins are proteins or glycoproteins that very specifically recognize and bind (poly)saccharides even in lipid- or protein-bound form.

The inventive microspheres for allergy therapy preferably have *Aleuria aurantia* lectin (AAL) on their microsphere surface.

Surface modification of the microspheres with *Aleuria aurantia* lectin causes selective enrichment and a prolongation of the dwell time of the microparticles in the intestine, thereby achieving a special therapeutical effect of the microparticles. *Aleuria aurantia* lectin (AAL) comes from an edible mushroom and binds to alpha-L-fucose of the so-called M cells. These M cells are derived from intestinal epithelial cells, with which they share surface properties such as carbohydrate structures (for example, alpha-L-fucose), and are part of the Peyer's patches, lymph organs of the intestine, which play a pivotal role for local antigen uptake and stimulation of the immune system. Further, a type of M cells can be detected in the nasal epithelium and used for mucosal targeting (Clark et al: Adv Drug Deliv Rev 2000 September 30; 43(2-3):207-23; or Brooking et al: J Drug Target 2001; 9(4):267-79).

The isolation and characterization of *Aleuria aurantia* lectin (AAL) is described in the book "The Lectins: Properties, Functions and Applications in Biology and Medicine" by I. E. Liener, N. Sharon and I. J. Goldstein (Academic Press 1986). Fucose binding lectin is isolated from the fruiting body of the orange peel fungus and was obtained for the example from Vector Laboratories (Burlingame, USA). It has a molecular weight of 72,000, the isoelectric point is between 9.0-9-2, and the lectin consists of 2 subunits of a single polypeptide chain of 31 kDa. AAL consists of two identical subunits each having a binding constant, $K_B$, of $6.1 \times 10^4$ $M^{-1}$ toward alpha-L-fucose.

The avidity (functional affinity) can be between $10^3$ and $10^7$ times stronger, due to multivalent bonds, than the corresponding affinity of a single binding site. The adhesion of the microspheres thus depends on the number of possibilities of binding between microspheres and epithelial cells, preferably on the number of lectin-to-cell bonds. That is, if the microsphere offers more than one possibility of binding the bond strength increases automatically, since in the case of a detachment all binding sites would have to be detached from epithelial cells at the same time. The avidity $K_B$ is preferably at least $1 \times 10^{10}$ $M^{-1}$, more preferably at least $1 \times 10^{11}$ $M^{-1}$ and most preferably at least $1 \times 10^{12}$ $M^{-1}$. It is furthermore preferred that the avidity of the microparticles is obtained by the multiplicity of AAL on the microparticles.

The inventive microspheres are used in allergy therapy. They are characterized in particular by the fact that they can accumulate in target-specific fashion in an elevated amount on mucosal surfaces of the gastrointestinal and/or nasal area and develop their therapeutical effect there. Therefore, the possibility of oral or nasal immunization is given. The advantages of such immunization lie in simple handling, which is also preferred by the patient. Since AAL is nontoxic, it is safe to use in humans and particularly preferred.

The microspheres preferably have a diameter of 0.1-100 μm, more preferably 0.1-10 μm and most preferably 0.2-5 μm. The size distribution of the microspheres was determined by means of laser diffraction (Shimadzu Laser Diffraction Type Particle Size Analyzer SALD-1100). It is apparent therefrom what maximum size 50 or 90% of the microspheres have. Microspheres smaller than 10 μm are preferably produced, because they can be more easily absorbed through intestinal epithelium. Microspheres smaller than 8 μm are more preferred, and microspheres smaller than 5 μm are most preferred.

Production of the micro- and/or nanospheres is usually done by the double emulsion technique or spray drying. In one of the following examples the production of corresponding particles will be described by way of example. Preferably, antigen-loaded microparticles are produced by dispersing the antigen in the aqueous solution into an organic solvent in which the polymer was dissolved. Various modifications of this process have already been described as methods of solvent evaporation (S. McClean, E. Prosser, E. Meehan, D. O'Malley, N. Clarke, Z. Ramtoola and D. Brayden, Binding and uptake of biodegradable poly-DL-lactide micro- and nanoparticles in intestinal epithelia, Eur J Pharm Sci 6 (1998) 153-163, R. K. Gupta, A. C. Chang, P. Griffin, R. Rivera, Y. Y. Guo and G. R. Siber, Determination of protein loading in biodegradable polymer microspheres containing tetanus toxoid, Vaccine 15 (1997) 672-678), extraction of water-in-oil-in-water emulsions (J. L. Cleland, E. T. Duenas, A. Park, A. Daugherty, J. Kahn, J. Kowalski and A. Cuthbertson, Development of poly-(D,L-lactide-coglycolide) microsphere formulations containing recombinant human vascular endothelial growth factor to promote local angiogenesis, J Control Release 72 (2001) 13-24, J. L. Cleland, A. Lim, A. Daugherty, L. Barron, N. Desjardin, E. T. Duenas, D. J. Eastman, J. C. Vennari, T. Wrin, P. W. Berman, K. K. Murthy and M. F. Powell, Development of a single-shot subunit vaccine for HIV-1. 5. programmable in vivo autoboost and long lasting neutralizing response, J Pharm Sci 87 (1998) 1489-1495), spray drying (N.E.S., N.W.A., Controlled release microparticles comprising core coated microparticles, U.S. patent, Biotek, Inc., Woburn, Mass., Nov. 18, 1986) or phase separation (F.J.W., Processes for preparation of microspheres, U.S. patent, Sandoz, Inc., E. Hanover, N.J., US, 1979).

The skeleton of the microspheres is preferably constructed from polymers with functional groups. The functional groups serve in particular to bind the force-mediating substances, particularly preferably lectins and most preferably AAL, to the surface of the particles chemically by a covalent bond, for example by an amide bond.

The antigens and/or DNA of antigens, preferably the allergens and/or DNA of allergens, can be incorporated into the micro- or nanospheres physically or chemically. They are preferably incorporated physically. As mentioned above, production of the micro- and/or nanospheres is preferably done by the double emulsion technique or spray drying. In the spray drying method, a solution of the polymer with an active agent dissolved, dispersed or emulsified therein is sprayed in a hot air stream. The solvent evaporates and causes the polymer to precipitate out, thereby embedding or encasing the active agent. The resulting microparticles are separated in a cyclone and obtained as powder. The polymer and active agent concentrations, the spray solution delivery rate, the inlet temperature, the atomizer air quantity and the aspirator power can be varied as parameters. The finer the produced drops are, the greater the active surface is and the better the heat transfer and substance transfer are.

In the production of the microspheres, an emulsion of ethyl formate/water with 5% polymer and 0.2% protein is preferably sprayed. The inlet temperature of the spray dryer is preferably 45° C. and the aspirator power is preferably set at 100%. The polymer is preferably dissolved in ethyl formate, and the proteins of the birch pollen extract preferably in water.

Functionalization of the micro- and/or nanospheres preferably takes place in two steps. In the first step, the free carboxyl groups on the surface of the microspheres, preferably PLGA microspheres, are activated by means of 1-ethyl-3-(3-dimethyl-aminopropyl) carbodiimide (EDAC) and (N-[2-hydroxyethyl-piperazine-N'-[2-ethanesulfonic acid]) (NHS) by a carbodiimide reaction. Subsequently, the lectin is coupled so as to form a stable amide bond.

Further preferably, the microspheres for allergy therapy consist of a skeleton comprising a biodegradable polymer or copolymer. This ensures that the particles can be degraded in the body. However, degradation must be delayed until the particles reach their destination and can continuously emit the antigens and/or DNA of antigens, preferably allergens and/or DNA of allergens, for a long time period. The biodegradability of the polymer or copolymer prevents the micro- or nanoparticles from being embedded in the body in an unwanted elevated concentration.

Particularly preferably, the skeleton of the microspheres for allergy therapy consists of polylactic acid (PLA), also known under the name of polylactide, polyglycolic acid (PGA), also known under the name of polyglycolide, or of poly(lactic-co-glycolic acid) copolymer (PLGA). These polymers can be slowly degraded into harmless substances in the body. Polylactides as administration systems for peptides and proteins are described in Johansen et al., European J. of Pharmaceutics and Biopharmaceutics 50 (2000): 129-146.

A conceivable microsphere skeleton is also chitosan, however, in particular for anionic allergens.

The micro- and/or nanospheres preferably contain 0.1-20 wt. %, particularly preferably 0.2-3 wt. %, of antigens and/or DNA of antigens. It is preferred that the wt. % values are values for allergens and/or DNA of allergens.

It is preferred that the micro- and/or nanospheres contain mimotopes of allergens, more preferably mimotopes of the allergen Phl p 5 and/or Bet v 1. It is particularly preferred that these are mimotopes of the allergen Phl p 5 and/or Bet v 1 with the amino acid sequences as defined above.

The present invention further relates to a method for producing above-described microspheres, characterized in that the microspheres have a binding constant $K_B$ of at least $1 \times 10^4$ $M^{-1}$ toward the specific carbohydrate residue of intestinal and/or nasal epithelial cells. The microspheres are constructed as described above.

The present invention further relates to the use of microspheres for allergy therapy, characterized in that the microspheres have a binding constant $K_B$ of at least $1 \times 10^{4+}$ $M^{-1}$ toward the specific carbohydrate residue of intestinal and/or nasal epithelial cells. The microspheres have a structure as described above. The avidity $K_B$ is preferably at least $10^{10}$ $M^{-1}$, more preferably $1 \times 10^{11}$ $M^{-1}$ and most preferably $1 \times 10^{12}$ $M^{-1}$.

An embodiment of the inventive microspheres will hereinafter be explained more closely by way of example with reference to the figures, in which:

FIG. 1 shows IgG titer against Bet v 1 after two-time oral immunization with microparticles; IgG detection is plotted against Bet v 1. ELISA plates were coated with recombinant Bet v 1, incubated with mouse sera (diluted 1:100), and bound IgG detected by peroxidase-labeled anti-mouse IgG. The reaction was visualized by addition of substrate, and reactivity measured with an ELISA reader. The values are directly proportional to the amount of bound antibody.

The abbreviations mean: MS=microspheres, BP=birch pollen extract, AAL=*Aleuria aurantia* lectin, WGA=wheat germ agglutinin, PIS=preimmune serum, 1.MIS=first immune serum, 2.MIS=second immune serum, OD=optical density.

FIG. 2 shows an examination of the antigenicity of birch pollen extract packaged into microspheres after gastric digestion; the graphic representation shows the antigenicity of the different microparticles in time dependence on gastric digestion. The abbreviations have the following meaning:

BP: birch pollen extract, MS: microspheres, AAL: *Aleuria aurantia* lectin, WGA: wheat germ agglutinin.

*Aleuria aurantia* lectin (AAL) has the advantage over many lectins of being nontoxic. A further, but toxic lectin is wheat germ agglutinin (WGA), which is thought to bind to intestinal epithelial cells due to its glycan-binding properties, in particular by binding to N-acetylglucosamine.

As shown in the examples described below, however, AAL has the further and unexpected advantage over WGA of binding significantly more antigen to the mucosal surface. This may be due to improved adhesion, but is in any case considered an advantage, since this property ultimately ensures that the allergens incorporated into the AAL-surface-modified microparticles can reach their therapeutical application site in target-specific fashion and in elevated quantity. Furthermore, repeated administration of increasing amounts of allergen at short intervals is unnecessary, because the microspheres are able to release the allergens into the target tissue slowly and continuously.

EXAMPLES

Example 1

Allergen-Containing, Lectin-Coupled PLGA Microspheres for Oral Allergy Prophylaxis and Therapy PLGA microspheres (MS) were obtained by means of spray drying. In this method, an emulsion of water and ethyl formate with birch pollen extract was sprayed in a hot air stream. The median of the microspheres was determined by means of laser diffraction and was 5.5 µm. The amount of protein in the microparticles was determined as 40 µg/mg microparticles. Functionalization of the microspheres with the particular lectins was done so as to form an amide bond. In the production of the microspheres an emulsion of ethyl formate/water with 5% (w/v) polymer and 0.2% (w/v) protein is sprayed. The polymer is dissolved in the ethyl formate, the proteins of the birch pollen extract in water. The emulsion is sprayed in a hot air stream. The solvent evaporates and causes the polymer to precipitate out, thereby embedding the proteins of the birch pollen extract. For protein determination, the microspheres were then dissolved in 0.05N NaOH/1% SDS and quantified by means of a staining test (bichinchoninic acid assay).

Functionalization of the micro- and/or nanospheres filled with proteins of the birch pollen extract is done in two steps. For this purpose, the particles are placed in HEPES buffer pH 7.2 and activated through addition of EDAC/NHS by a carbodiimide reaction. AAL is added and the lectin coupled to the micro- and/or nanospheres through formation of a stable amide bond. The remaining activated carboxyl groups are saturated with glycine.

Figure 1:
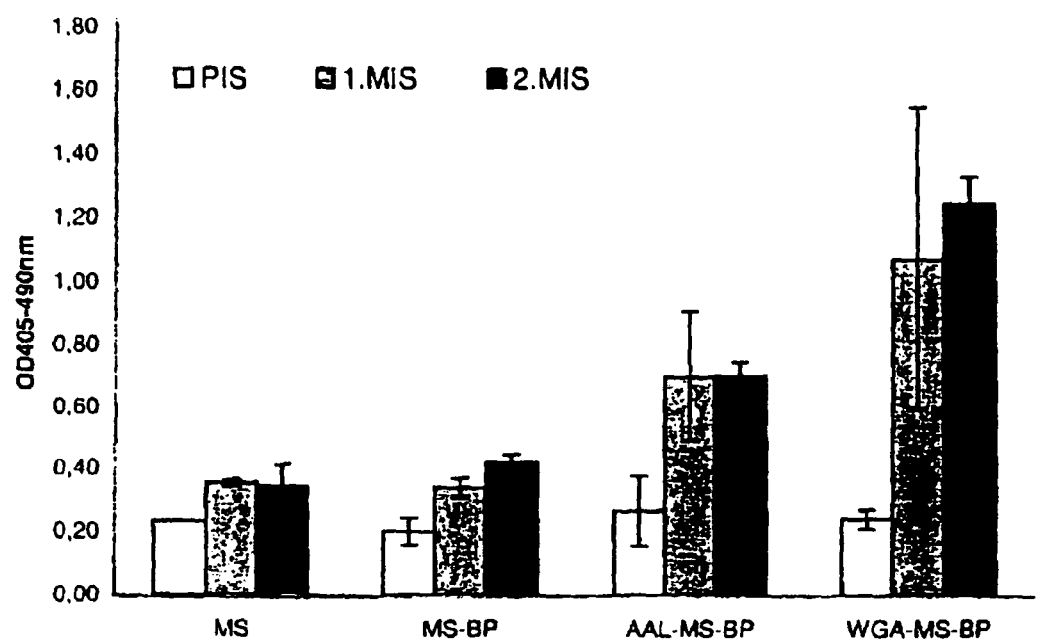

The results of the immunization model are shown in FIG. 1. Four groups of 5 BALB/c mice each were immunized intragastrically with microparticles in PBS (volume 150 microL) twice (day 0 and day 21) on three consecutive days in each case. The microparticles were either empty or packed with birch pollen proteins. A part of the microparticles that were packed with birch pollen proteins was furthermore functionalized additionally with *Aleuria aurantia* lectin or wheat germ agglutinin. Before and two weeks after the immunizations, blood was taken from the mice and examined for presence of specific anti-Bet v 1 antibodies. This was done by ELISA. Birch pollen extract was coated in a concentration of 10 microg/ml of carbonate buffer, pH 9.6. After blocking with PBS/0.1% BSA, mouse sera (diluted 1:100 in blocking buffer) were incubated. After washing with PBS, bound IgG was detected with anti-mouse antibodies, peroxidase conjugated. The reaction was developed by addition of substrate, and the evaluation done by reading at OD 405-490 nm in an ELISA reader.

As can be seen in FIG. 1, the groups fed with empty or birch pollen protein-packed microparticles did not show a relevant increase of Bet v 1 specific IgG antibodies over the preimmune serum by ELISA either in the first immune serum (1.MIS—gray bar) or in the second immune serum (2.MIS—gray-black bar). However, both groups in which the packed microparticles were additionally functionalized externally with lectins showed a clear increase in IgG antibodies aimed at Bet v 1.

Example 2

Gastric Digestion

To examine the antigenicity of microsphere-packed birch pollen extract (BP-MS) after gastric digestion, microspheres were incubated with pepsin at pH 1.5 for different time intervals. Birch pollen protein packaged into microspheres could be detected antigenetically even after two hours of digestion, while non-packaged birch pollen protein was destroyed within seconds. AAL-coupled microparticles reacted in this experiment just as advantageously as other microsphere preparations (MS: microspheres alone, MS-WGA: microspheres coupled with wheat germ agglutinin) and protected the protein from digestion. This example further shows that birch pollen protein loses none of its antigenicity compared to untreated extracts when packaged into microspheres.

Figure 2:
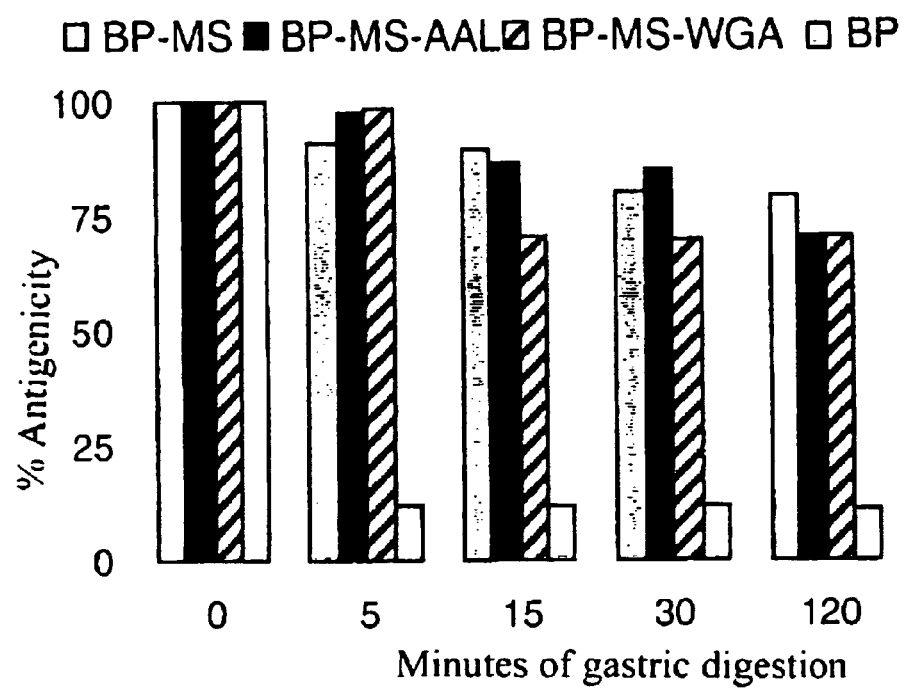

Evaluation of the experiment was done in an ELISA: birch pollen protein was extracted from microspheres and the solution used for coating ELISA plates. Bound birch pollen main allergen Bet v 1 was detected with a polyclonal rabbit anti-Bet v 1 antibody and then by means of a second peroxidase-labeled anti-rabbit IgG antibody. The reaction was visualized by addition of substrate, and the signal measured in an ELISA reader. The bound antigen is directly proportional to the reactivity and therefore to the signal. The results are shown graphically in FIG. 2.

Example 3

Qualitative Adhesion of Different Microsphere Preparations

Qualitative examination of the adhesion of different microsphere preparations to human intestinal epithelial cells was done by the immunofluorescence method. The cell line Caco-2 was seeded onto glass plates and incubated at 4° C. with:
1. Birch pollen extract packaged into microspheres (BP-MS), or
2. Birch pollen extract packaged into microspheres, coupled with wheat germ agglutinin (BP-WGA-MS), or
3. Birch pollen extract packaged into microspheres, coupled with *Aleuria aurantia* lectin (BP-AAL-MS).

For visualization, the microspheres were loaded with the fluorescence dye, fluorescein isothiocyanate (FITC) cadaverine. Visualization of the epithelial cells was done with a rabbit anti-PLAP antibody, followed by Alexa 568-conjugated anti-rabbit IgG. The cell nuclei were dyed with Hoechst dye.

Figure 3:
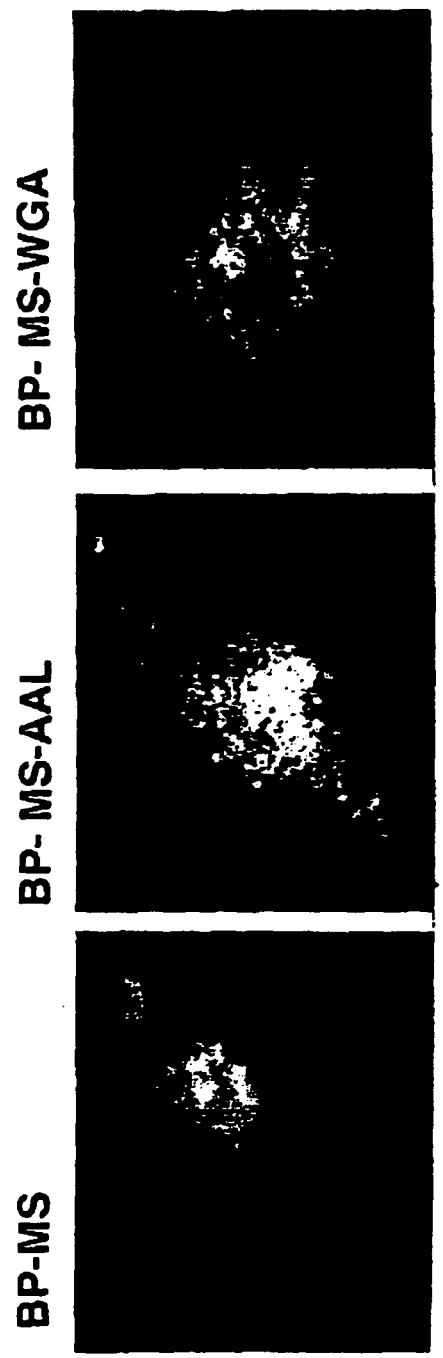
FIG. 3 shows a qualitative examination of the adhesion of different microsphere preparations to human intestinal epithelial cells by immunofluorescence.

Compared to non-functionalized microspheres, this experiment makes it clear that lectin functionalization significantly improves the connection of the particles to the epithelium. The results are shown in FIG. 3.

Example 4

Quantitative Examination of Adhesion of Different Microsphere Preparations

The quantitative examination of the adhesion of different microsphere preparations to human intestinal epithelial cells was done by fluorescence ELISA. The cell line Caco-2 was grown in 96-well tissue culture plates until it formed closed single-layered sheets. Incubation was then effected at 4° C. with:
1. Birch pollen extract packaged into microspheres (BP-MS), or
2. Birch pollen extract packaged into microspheres, coupled with wheat germ agglutinin (BP-WGA-MS), or
3. Birch pollen extract packaged into microspheres, coupled with *Aleuria aurantia* lectin (BP-AAL-MS).

For visualization, microspheres labeled with FITC cadaverine were used. Visualization of the epithelial cells was done by fluorescence detection at 485/535 nm. The signal is directly proportional to the number of bound particles.

Figure 4:
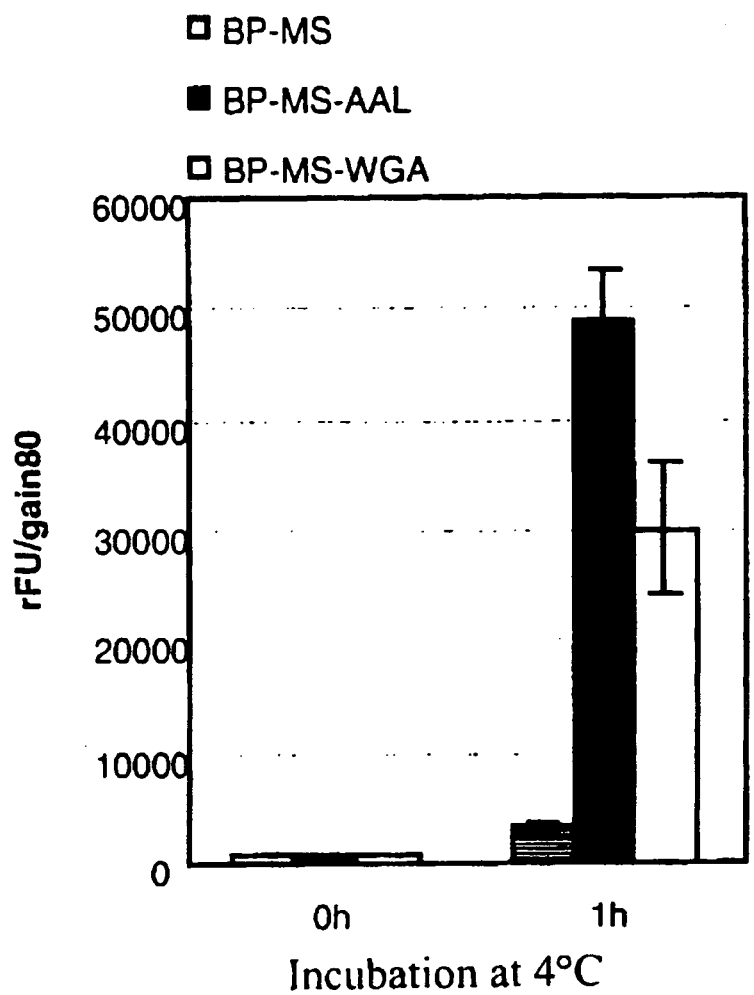
FIG. 4 shows a quantitative examination of the adhesion of different microsphere preparations to human intestinal epithelial cells by fluorescence ELISA.

Compared to non-functionalized microspheres, this experiment makes it clear that lectin functionalization significantly improves the connection of the particles to the epithelium. But above all, AAL has considerably increased adhesion compared to WGA. The results are shown in FIG. 4.

The invention claimed is:

1. Polymeric microspheres comprising:
   *Aleuria aurantia* lectin; and
   an extract of pollen or a mimotope of Phl p5 as set forth in SEQ ID NOs: 1-16 or Bet v1 as set forth in SEQ ID NO: 17, or a combination thereof;
   wherein the *Aleuria aurantia* lectin is on the surface of the polymeric microspheres and the extract of pollen or the mimotope is contained within the polymeric microspheres.

2. The polymeric microspheres of claim 1, wherein the extract of pollen comprises an extract of birch pollen, an extract of alder pollen, an extract of grass pollen, or a combination thereof.

3. The polymeric microspheres of claim 1, wherein the polymeric microspheres have a diameter of from 0.1 to 100 μm.

4. The polymeric microspheres of claim 1, wherein the polymeric microspheres comprise polymers containing functional groups.

5. The polymeric microspheres of claim 1, wherein the polymeric microspheres comprise biodegradable polymers.

6. The polymeric microspheres of claim 4 or claim 5, wherein the polymers are polylactic acid, polyglycolic acid or of poly(lactic-co-glycolic acid) copolymer.

7. The polymeric microspheres of claim 1, wherein the *Aleuria aurantia* lectin is bound to polymers of the polymeric microspheres by a covalent bond.

8. A method for producing the polymeric microspheres of claim 1 comprising loading the extract of pollen or the mimotope into the polymeric microspheres, functionalizing the polymeric microspheres, and coupling *Aleuria aurantia* lectin to the surface of the polymeric microspheres.

9. A method of treating an allergy comprising administering the polymeric microspheres of claim 1 to a subject in need of allergy therapy.

10. The polymeric microspheres of claim 1, wherein the extract of pollen comprises Bet v1.

11. The polymeric microspheres of claim 2, wherein the extract of pollen comprises Phl p1, Phl p5, Phl p6, or Phl p7.

* * * * *

UNITED STATES PATENT AND TRADEMARK OFFICE
CERTIFICATE OF CORRECTION

| | |
|---|---|
| PATENT NO. | : 8,420,095 B2 |
| APPLICATION NO. | : 10/562066 |
| DATED | : April 16, 2013 |
| INVENTOR(S) | : Erika Jense-Jarolim et al. |

Page 1 of 1

It is certified that error appears in the above-identified patent and that said Letters Patent is hereby corrected as shown below:

Title Page, Item (73) Assignee: please delete "Biomay Produktions-und Handels AG" and insert therefor -- Biomedical International R + D GmbH --.

Signed and Sealed this
Thirteenth Day of August, 2013

Teresa Stanek Rea
*Acting Director of the United States Patent and Trademark Office*